US00PP33270P3

(12) United States Plant Patent
Gray et al.

(10) Patent No.: US PP33,270 P3
(45) Date of Patent: Jul. 20, 2021

(54) FLORIBUNDA ROSE PLANT NAMED 'GRAPSTG'

(50) Latin Name: ***Rosa* hybrid**
Varietal Denomination: GRApstg

(71) Applicants: John Charles Gray, Highfields (AU); Sylvia Elizabeth Gray, Highfields (AU)

(72) Inventors: John Charles Gray, Highfields (AU); Sylvia Elizabeth Gray, Highfields (AU)

( * ) Notice: Subject to any disclaimer, the term of this patent is extended or adjusted under 35 U.S.C. 154(b) by 7 days.

(21) Appl. No.: 16/873,187

(22) Filed: Feb. 24, 2020

(65) Prior Publication Data

US 2020/0275595 P1 Aug. 27, 2020

Related U.S. Application Data

(60) Provisional application No. 62/809,213, filed on Feb. 22, 2019.

(51) Int. Cl.
*A01H 5/02* (2018.01)
*A01H 6/74* (2018.01)

(52) U.S. Cl.
USPC ..... Plt./143
CPC ..... *A01H 6/749* (2018.05)

(58) Field of Classification Search
USPC ..... Plt./143
CPC ..... A01H 5/0222
See application file for complete search history.

(56) References Cited

PUBLICATIONS http://www.rose.org.au/assets/oznames-11-11-2018.pdf; Nov. 11, 2018; 2 pages.*

* cited by examiner

*Primary Examiner* — Kent L Bell
(74) *Attorney, Agent, or Firm* — Samuel R. McCoy, Jr.

(57) ABSTRACT

'GRApstg' is a new and distinct floribunda type *Rosa* hybrid plant which is characterized by the combination of an upright growth habit, good resistance to *Diplocarpon rosae* and *Podosphaera pannosa,* nearly continuous flowering, flowers exhibit distinct pink with cream stripes and flecks and petal reverse pink with cream stripes and flecks, a very strong rose fragrance, and the stability of these characteristics from generation to generation. The new cultivar is generally suited to landscape applications.

2 Drawing Sheets

Latin name of genus and species: The Latin name of the genus and species of the novel variety disclosed herein is *Rosa* hybrid.

Variety denomination: The inventive variety of *Rosa* hybrid disclosed herein has been given the variety denomination 'GRApstg'.

BACKGROUND OF THE INVENTION

Parentage: 'GRApstg' is a seedling selection which resulted from the controlled cross-pollination of *Rosa* hybrid 'Grace' (not patented) and an unnamed *Rosa* hybrid male breeding line (not patented). Both parents, developed by the same inventor and never commercially released, exhibited traits deemed commercially significant and desirable.

After many years of trialing, the female parent was confirmed to possess a combination of desirable traits such as very strong fragrance, very high resistance to powdery mildew, and having flowers that are pink with cream stripes and flecks borne on a bushy plant growing to 1.2 meters tall and 1 meter wide. The male parent was selected for use in breeding after trialing confirmed the presence of a modern flower color. During the spring of 2015, the female parent was emasculated and was manually pollinated with pollen from the male parent. In autumn of 2016, seed was collected from hips produced by the female parent and a number of seedlings were grown to a mature size, including the claimed plant. These progeny were further evaluated for desirable traits such as fragrance, mildew disease resistance and original flower color, and in January of 2016 the claimed plant was first observed. In January of 2017, after further evaluation for desirable traits, the claimed plant was deemed to be garden-worthy and suited to widespread cultivation. It was given the denomination, 'GRApstg'.

Asexual Reproduction: Asexual propagation of 'GRApstg', by way of softwood stem cuttings, was first performed in May of 2016 at the inventor's nursery in Highfields, Australia. Through more than twelve subsequent generations, the unique features of this cultivar have proven to be stable and true to type.

SUMMARY OF THE INVENTION

The following characteristics have been repeatedly observed and represent the distinguishing characteristics of the new *Rosa* cultivar 'GRApstg'. These traits, in combination, distinguish 'GRApstg' as a new and distinct cultivar.

1. *Rosa* hybrid 'GRApstg' exhibits an upright growth habit; and
2. *Rosa* hybrid 'GRApstg' exhibits high resistance to the plant pathogen, *Podosphaera pannosa*, commonly referred to as rose powdery mildew disease; and
3. *Rosa* hybrid 'GRApstg' exhibits repeat flowering; and 4. *Rosa* hybrid 'GRApstg' exhibits a double flower type; and
5. *Rosa* hybrid 'GRApstg' exhibits flowers that are pink with cream stripes and flecks; and
6. *Rosa* hybrid 'GRApstg' exhibits flowers with a very strong rose fragrance.

DETAILED BOTANICAL DESCRIPTION

Figure 1:
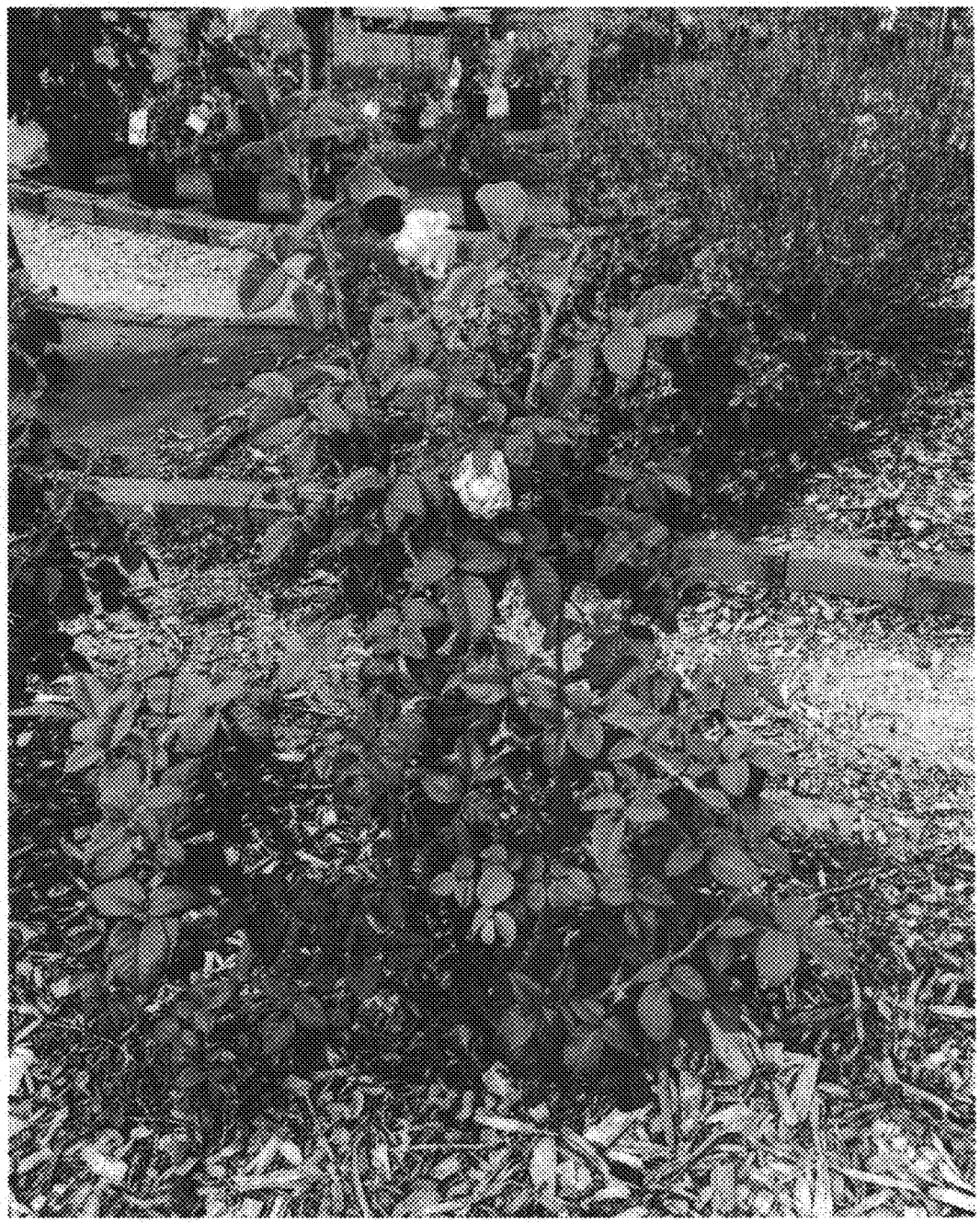
FIG. 1 illustrates, as nearly true as it is reasonably possible to make the same in color photographs of this type, an exemplary 12 month old 'GRApstg' plant grown outdoors at the inventor's commercial nursery in Highfields, Australia.
Figure 2:
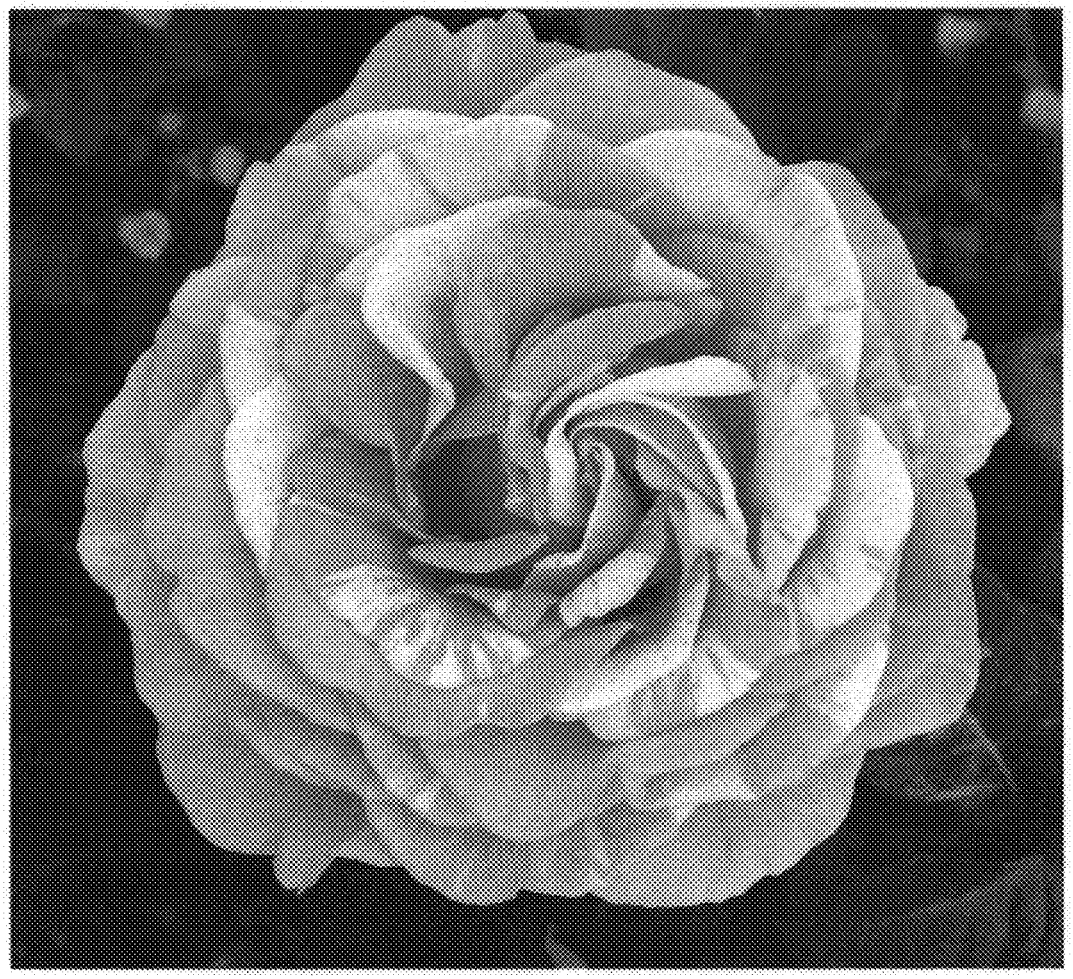
FIG. 2 illustrates, as nearly true as it is reasonably possible to make the same in color photographs of this type, the typical flower of 'GRApstg'.

The following observations and measurements, made in February of 2019, describe averages of two own-root specimens of one year old 'GRApstg' plants. The plants were grown outdoors in a garden bed of a red krasnozem soil in full sunlight, at the inventor's nursery in Highfields, Australia. No shade or supplemental light was provided. Temperatures ranged from approximately 17 to 35 degrees Celsius during the day and 7 to 18 degrees Celsius at night. Standard practices for irrigation, fertilizer and pest control were applied at appropriate times during the growing season. The plants were pruned three times during the growing season using accepted techniques for rose pruning.

Those skilled in the art will appreciate that certain characteristics will vary with older or, conversely, with younger plants. 'GRApstg' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2007 Fifth Edition except where common terms of color are used.

A botanical description of 'GRApstg' and comparisons with the parents and the most similar commercial cultivar of *Rosa* hybrid are provided below.

General plant description:

*Growth habit.*—Upright.

*Growth rate.*—Approximately 6 months to reach 60 cm.

*Dimensions.*—100 cm tall and 60 cm wide.

*Environmental tolerance.*—Very good heat tolerance; cold hardiness is unknown.

*Disease resistance.*—Excellent resistance to powdery mildew (*Sphaerotheca pannosa*) and good resistance to blackspot (*Diplocarpon Rosae*).

*Pest resistance.*—Neither resistance nor susceptibility to typical *Rosa* sp. pests has been observed.

*Propagation.*—Technique — Softwood stem cuttings. Time to initiate roots — About 13 days at approximately 21 degrees Celsius at root zone and 18 degrees Celsius ambient temperature. Time to produce a rooted cutting — About 25 days at approximately 21 degrees Celsius at root zone and 18 degrees Celsius ambient temperature.

Root system: White fibrous roots with many root hairs extending from lesser roots in a featherlike arrangement.

Branches:

*Branching habit.*—Irregular branching from mature branches, breaking first from the uppermost buds near the apex of each shoot.

*Quantity.*—Numerous.

*General dimensions.*—Approximately 60 cm long; 1.5 cm in diameter near the base and tapering to 0.5 cm.

*Immature branches.*—Length — 25 cm. Diameter — Approximately 0.5 cm. Texture and pubescence — Glabrous, with prickles. Color — Nearest to RHS 135D. Prickles — Density — Sparse to moderate; 3 prickles per 2.5 cm of branch. Color — Nearest to RHS 151D. Shape — Convex. Texture — Smooth.

*Mature branches.*—Length — 40 cm. Diameter — Approximately 1.5 cm, after one year. Texture and pubescence — Glabrous, with prickles. Color — Nearest to RHS 144B. Prickles — Density — Sparse to moderate; 3 prickles per 2.5 cm of branch. Color — Nearest to RHS N172D. Shape — Convex. Texture — Smooth.

Leaves:

*Arrangement.*—Alternate imparipinnate compound leaves.

*Quantity.*—Approximately 5 per mature branch.

*Attachment.*—Petiolate.

*Leaf internode length.*—4 cm.

*Dimensions.*—Approximately 12 cm long and 70 cm wide.

*Petiole.*—Dimensions — 2.5 cm long and 0.1 to 0.2 cm wide. Color — Near RHS 145A and margined RHS 143B. Texture and pubescence — Smooth, glabrous. Prickles — Present. Stipitate glands — Not present.

*Stipule.*—Shape — Linear to lanceolate. Dimensions — 1.5 cm long and 0.5 cm wide. Color — Nearest to RHS 141C. Texture and pubescence — Smooth, glabrous. Margins — Ciliate. Apex — Apiculate. Base — Winged. Prickles — Not present. Stipitate glands — Not present.

*Rachis.*—Dimensions — 2.0 cm long and 0.1 cm wide. Color — Near RHS 144C. Prickles — Present. Stipitate glands — Not present.

*Leaflets.*—Quantity — Seven leaflets on axillary leaves. Dimensions — Average size of the terminal leaflet is 4 cm long and 2 cm wide. Shape — Ovate. Apex — Acuminate. Base — Ovate. Margins — Serrated. Texture, pubescence and luster, adaxial surface — Bullate, glabrous, and matte. Texture, pubescence and luster, abaxial surface — Bullate, glabrous, and matte. Juvenile foliage color, adaxial surface — Nearest to RHS N144C, with no anthocyanin intonations. Juvenile foliage color, abaxial surface — Nearest to RHS 144D, with anthocyanin intonations, nearest to RHS 71A. Mature foliage color, adaxial surface — Nearest to RHS 141B. Mature foliage color, abaxial surface — Nearest to RHS 141D. Venation — Pinnate. Venation color, adaxial surface — Nearest to RHS 141A, with midrib RHS 144B. Venation color, abaxial surface — Nearest to RHS 142B, with midrib RHS 142C.

*Petiolule*.—Dimensions — 0.4 cm long and 0.1 cm wide. Color — Near RHS N142B, with no anthocyanin intonations present. Prickles — Not present. Texture — Smooth.

Inflorescence:

*Inflorescence type*.—Flowers are single or clustered.

*Blooming habit*.—Almost continuous from October through June in the southern hemisphere.

*Time to flower*.—6 to 8 weeks for a new stem to mature and flowering begins to occur once a stem matures.

*Peduncle*.—Dimensions — 45 cm long and 0.3 cm in diameter. Color — Nearest to RHS 144C. Strength — Strong. Texture and pubescence — Smooth, glabrous. Prickles — Not present.

Bud:

*Shape*.—Ovate.

*Size*.—2.0 cm long and 2.0 cm in diameter.

*Color*.—Nearest to RHS 142B.

Flower:

*Pedicels*.—Dimensions — 3.5 cm lnog and 0.1 cm in diameter. Color — Nearest to RHS 135D. Strength — Moderately strong. Texture and pubescence — Smooth and glabrous. Prickles — None present.

*Calyx*.—General — Comprised of five polysepalous sepals. Diameter of calyx — 1.0 cm.

*Sepals*.—Shape — Lanceoalate; occasionally with leafy appendages. Color, interior surface — RHS 142D. Color, exterior surface — RHS 141D. Dimensions — 2.0 cm long and 1.0 cm wide. Apex — Apiculate. Base — Flat at union with receptacle. Quantity — Five. Pubescence — Densely puberulent. Margins — Entire. Stipitate glands — None present.

*Corolla*.—General shape of corolla — Cupped and irregularly-rounded with a tight outer whorl. Rate of opening — 6 days from bud to anthesis. Dimensions — Approximately 8 cm in diameter and 5 cm deep. Fragrance — strong rose scent. Lastingness — On the plant for 5 days after anthesis. Persistence — Self-cleaning. Petals — Petal count — Exhibits double flowers with approximately 70 petals under normal conditions. Petal arrangement — Irregularly rounded whorl at anthesis and aging to a loose whorl. Dimensions — 4.5 cm long and 3.5 cm wide. Petal shape — Obovate. Apex — Rounded. Base — Flattened, then obtuse. Petal reflex — Slightly reflexed at apex. Petal margin — Entire; slightly undulating. Texture — Soft. Aspect — Formal. Petal color, upon opening — Upper surface — Nearest to RHS 55A, with base nearest to RHS 9A, and striped and flecked nearest to RHS 9D. Lower surface — Nearest to RHS 38C, with base nearest to RHS 9A. Petal color, at anthesis — Upper surface — Nearest to RHS 38D, with base near RHS 9A. Lower surface — Nearest to RHS 37D, with margin nearest to RHS 49D. Fading — Nearest to RHS 13D.

Reproductive organs:

*Stamens*.—Quantity — Approximately 50. Anthers — Shape — Narrow ovate. Length — 1.0 cm. Color — Nearest to RHS 12A. Pollen — Many. Pollen Color — Nearest to RHS 3A.

*Filaments*.—Color — Nearest to RHS 17C. Length — Approximately 0.8 cm.

*Pistils*.—Quantity — Approximately 50. Length — Approximately 1.0 cm. Stigma — Position — Held level at one-quarter the length of the filament and anther. Shape — Ovate. Color — Near RHS 11B. Style — Length — Approximately 0.8 cm long. Color — Nearest to RHS 18C.

*Ovary*.—Dimensions — 0.5 cm long and 0.3 cm wide. Color — Nearest to RHS 3D.

*Receptacle*.—Shape — Pitcher-shaped. Dimensions — 0.5 cm high and 0.5 cm wide. Color — Nearest to RHS 141D.

Hip and seed:

*Hip*.—Shape — Rounded. Dimensions — 1.0 cm long and 1.0 cm wide. Texture — Smooth. Color — Nearest to RHS 149C.

*Seed*.—Shape — Rounded. Dimensions — 1.0 cm long and 1.0 cm wide. Color — Nearest to RHS 144D.

COMPARISONS WITH THE PARENTS

The new rose plant 'GRApstg' may be distinguished from its seed parent, *Rosa* hybrid 'Grace', by the following combination of characteristics:

1. The flowers of 'GRApstg' exhibit a distinct pink with cream stripes and flecks and petal reverse pink with cream stripes and flecks, whereas the flowers of the seed parent exhibit a pink general coloration.
2. 'GRApstg' exhibits an upright growth habit, whereas the seed parent exhibits an upright to semi weeping growth habit.

The new rose plant 'GRApstg' may be distinguished from its pollen parent, an unnamed breeding line, by the following combination of characteristics:

1. The flowers of 'GRApstg' exhibit a distinct pink with cream stripes and flecks and petal reverse pink with cream stripes and flecks, whereas the flowers of the pollen parent exhibit a yellow color with pink stripes and flecks general coloration.
2. 'GRApstg' exhibits a very high powdery mildew resistance, whereas the pollen parent is susceptible.

COMPARISONS WITH THE MOST SIMILAR VARIETY OF COMMON KNOWLEDGE

Plants of the new cultivar 'GRApstg' may be distinguished from the commercial variety *Rosa* hybrid 'MACoranlem' (not patented) by the following combination of characteristics:

1. The flowers of 'GRApstg' exhibit a distinct cream stripes and flecks and petal reverse pink with cream stripes and flecks, whereas the flowers of 'MACoranlem' are orange striped with lemon yellow.
2. Leaves of 'GRApstg' are bullate, glabrous, and matte mid-green whereas leaves of 'MACoranlem' are glossy dark green.
3. 'GRApstg' has flowers with very strong fragrance whereas 'MACoranlem' flowers have mild fragrance.

That which is claimed:

1. A new and distinct variety of *Rosa* hybrid plant named 'GRApstg', as described and illustrated herein.

* * * * *